United States Patent
Dreyfuss et al.

(10) Patent No.: US 8,343,186 B2
(45) Date of Patent: Jan. 1, 2013

(54) FULLY THREADED SUTURE ANCHOR WITH TRANSVERSE ANCHOR PIN

(75) Inventors: Peter J. Dreyfuss, Naples, FL (US); William C. Benavitz, Naples, FL (US)

(73) Assignee: Arthrex, Inc., Naples, FL (US)

( * ) Notice: Subject to any disclaimer, the term of this patent is extended or adjusted under 35 U.S.C. 154(b) by 678 days.

(21) Appl. No.: 11/097,172

(22) Filed: Apr. 4, 2005

(65) Prior Publication Data

US 2005/0222618 A1    Oct. 6, 2005

Related U.S. Application Data

(60) Provisional application No. 60/559,425, filed on Apr. 6, 2004.

(51) Int. Cl.
A61B 17/04 (2006.01)
(52) U.S. Cl. ....................................................... 606/232
(58) Field of Classification Search .................. 606/232, 606/72–74, 300, 309, 312; 411/320, 142, 411/199, 216, 356, 357, 76, 340, 555
See application file for complete search history.

(56) References Cited

U.S. PATENT DOCUMENTS

| | | | |
|---|---|---|---|
| 4,632,100 A | 12/1986 | Somers et al. | |
| 5,156,616 A | 10/1992 | Meadows et al. | |
| 5,370,662 A | 12/1994 | Stone et al. | |
| 5,964,783 A | 10/1999 | Grafton et al. | |
| 6,511,499 B2 | 1/2003 | Schmieding et al. | |
| 6,923,824 B2 | 8/2005 | Morgan et al. | |
| 7,322,978 B2 | 1/2008 | West, Jr. | |
| 2002/0052629 A1 | 5/2002 | Morgan et al. | |
| 2002/0147463 A1* | 10/2002 | Martinek | 606/232 |
| 2003/0065361 A1* | 4/2003 | Dreyfuss | 606/232 |
| 2004/0133239 A1* | 7/2004 | Singhatat | 606/232 |
| 2005/0283158 A1 | 12/2005 | West, Jr. | |

* cited by examiner

Primary Examiner — Dianne Dornbusch
(74) Attorney, Agent, or Firm — Carlson, Gaskey & Olds, P.C.

(57) ABSTRACT

A suture anchor has a pin that is disposed transversely within the suture anchor, over which one or more strands of suture is looped. The anchor body is threaded and has a tapered distal portion. The proximal end portion of the suture anchor body has a hexagonally shaped opening to accept a hexagonal drive head. The peripheral surface defining hexagonally shaped opening is rounded and smooth to prevent abrading sutures placed in contact therewith.

20 Claims, 4 Drawing Sheets

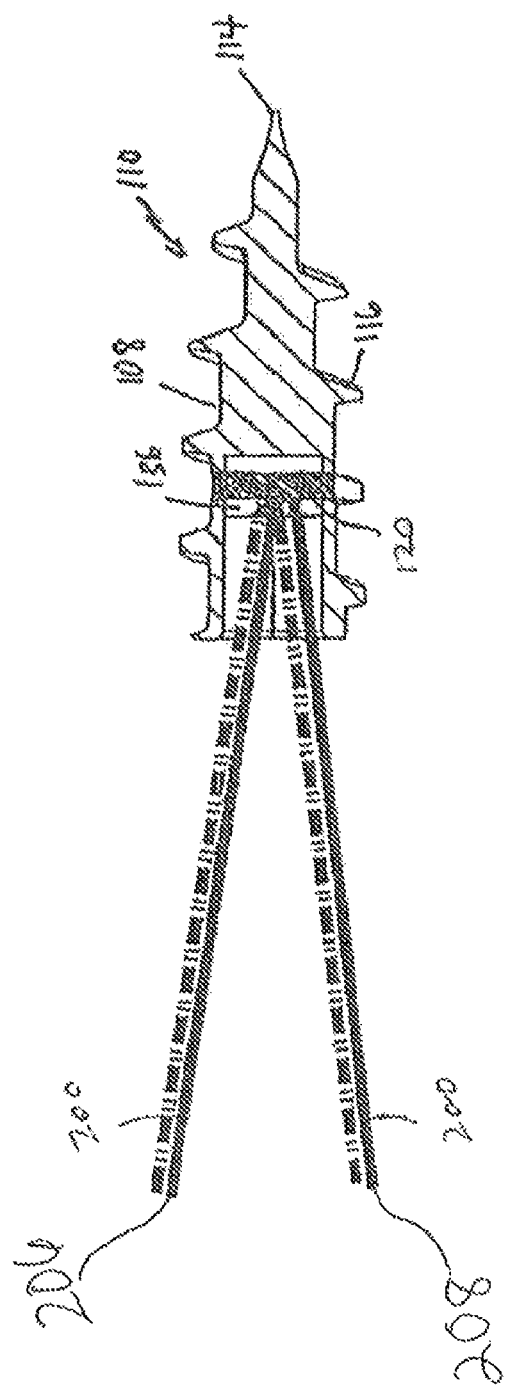

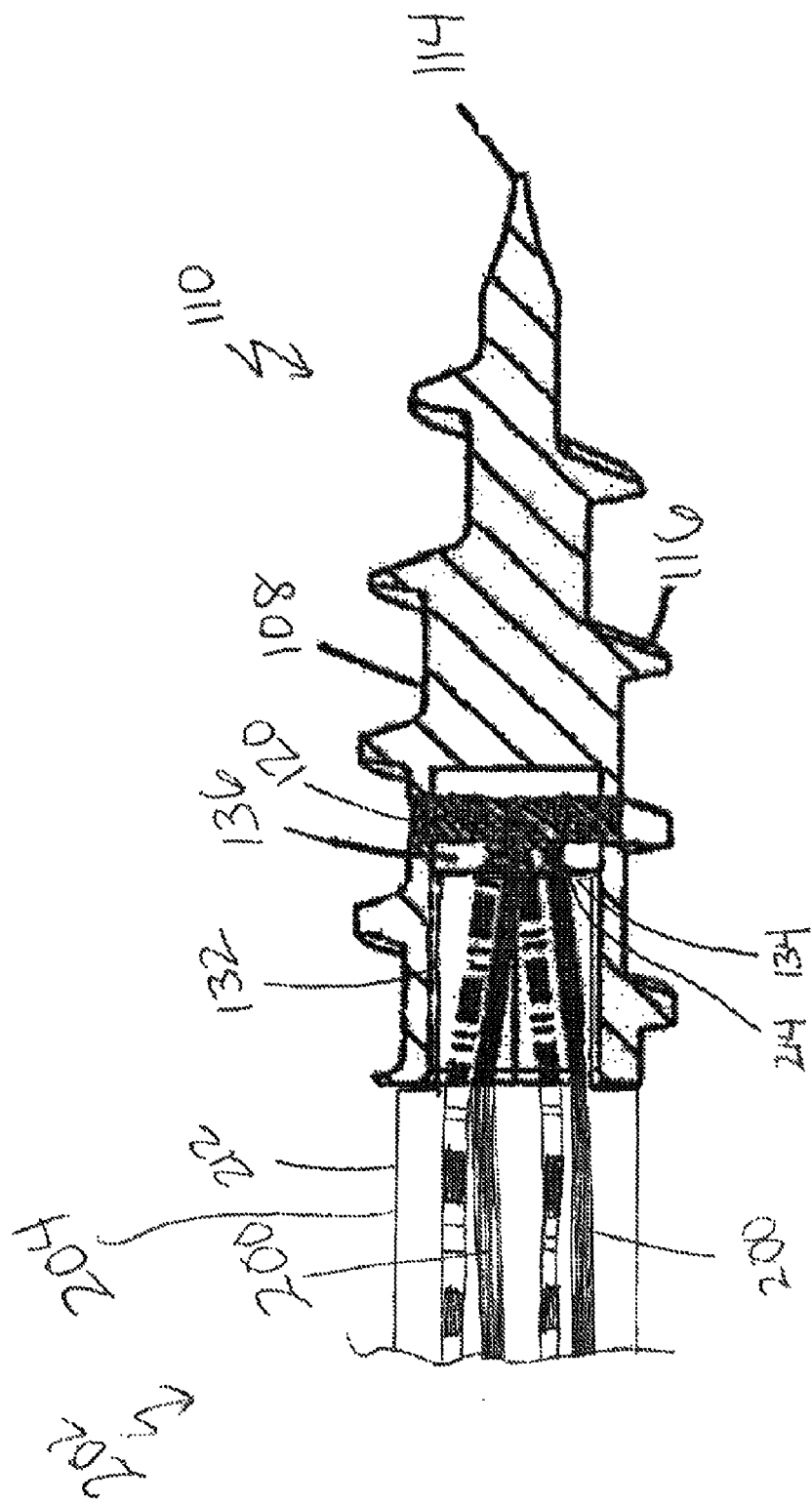

FULLY THREADED SUTURE ANCHOR WITH TRANSVERSE ANCHOR PIN

This application claims the benefit of U.S. Provisional Application No. 60/559,425, filed Apr. 6, 2004, the entire disclosure of which is incorporated by reference herein.

FIELD OF THE INVENTION

The present invention relates to an apparatus for anchoring surgical suture to bone. More specifically, the present invention relates to a fully threaded suture anchor provided with a transverse anchor pin for securing, within the anchor, one or more strands of suture to anchor the suture to bone during arthroscopic surgery.

When soft tissue tears away from bone, reattachment becomes necessary. Various devices, including sutures alone, screws, staples, wedges, and plugs have been used in the prior art to secure soft tissue to bone.

Recently, various types of threaded suture anchors have been developed for this purpose. Some threaded suture anchors are designed to be inserted into a pre-drilled hole. Other suture anchors are self-tapping.

U.S. Pat. No. 4,632,100 discloses a cylindrical threaded suture anchor. The suture anchor of the '100 patent includes a drill bit at a leading end for boring a hole in a bone, followed by a flight of threads spaced from the drill bit for securing the anchor into the hole created by the drill bit.

U.S. Pat. No. 5,370,662 discloses a suture anchor having threads which extend to the tip of the anchor. U.S. Pat. No. 5,156,616 discloses a similar suture anchor having an axial opening for holding a knotted piece of suture.

All of the above-noted suture anchors include structure for attaching the suture to the anchor. U.S. Pat. No. 4,632,100, for example, discloses a press-fitted disc and knot structure which secures the suture to the anchor. In other suture anchors, such as those disclosed in U.S. Pat. No. 5,370,662, the suture is passed through an eyelet located on the proximal end of the anchor. In the case of a bioabsorbable suture anchor, the suture may be insert molded into the anchor, as disclosed in U.S. Pat. No. 5,964,783.

Problems can arise if the structure for attaching the suture fails, allowing the suture to become detached from the anchor. Also, the suture often is exposed to abrasion or cutting by sharp or rough areas along the walls of the bone canal into which the anchor is inserted.

Moreover, the eyelet or, in the case of U.S. Pat. No. 4,632,100, the axial opening for receiving the disc to which the suture is knotted, is formed as part of the drive head of the known suture anchors. Combining these two functions in one structure often tends to weaken the drive head.

In addition, various other modifications to the drive head often are employed in connection with suture attachment. For example, recessed grooves may be formed on opposite sides of the drive head to receive and protect the suture from abrasive areas of the suture anchor tunnel or to facilitate mating between the anchor to the driver. In such cases, the drive head often must be made of a larger diameter to recover the mechanical strength lost from the removal of material relating to the suture-attachment or suture-protection modifications.

Further, the prior art suture anchors having eyelets extending from the proximal ends require countersinking of the eyelet below the bone surface to avoid having the patient's tissue abrade against the exposed eyelet. As a result, suture attached to the eyelet is vulnerable to abrasion by the bony rim of the countersunk hole into which the suture anchor is installed. In addition, in biodegradable suture anchors, the suture eyelet can degrade rapidly, causing the suture to become detached from the anchor prematurely.

Accordingly, there is a need for a threaded suture anchor to which suture is secured effectively so as to prevent detachment of the suture. It is further desirable for such suture anchors to have eyelets that will not abrade tissue and which do not require countersinking.

SUMMARY OF THE INVENTION

The suture anchor of the present invention overcomes the disadvantages of the prior art discussed above by providing a threaded suture anchor having a tranverse anchor pin disposed inside the body of the suture anchor. The suture anchor is made of a biocompatible metal, preferably a titanium alloy.

The proximal end surface of the threaded suture anchor of the present invention is preferably smooth and rounded to minimize suture abrasion, while the distal portion of the anchor is tapered to an elongated point to enable the anchor to be self-tapping. The proximal end portion of the suture anchor body has a hexagonally shaped opening to accept a hexagonal drive head.

The internal transverse pin provides a support over which one or more strands of suture can be looped, such that the suture is secured in a recessed fashion within the anchor.

Advantageously, suture attached to the anchor through the transverse pin exits the suture anchor through a central bore in the anchor, which prevents suture abrasion by the wall of the bone tunnel into which the anchor is inserted.

Other features and advantages of the present invention will become apparent from the following description of the invention, which refers to the accompanying drawings.

BRIEF DESCRIPTION OF THE DRAWINGS

FIG. 4 is a cross sectional view of the suture anchor of FIG. 1 showing a suture looped over the transverse anchor pin.

FIG. 5 is a cross sectional view of the suture anchor of FIG. 1 showing a portion of a hex driver inserted into a hexagonally shaped bore.

DETAILED DESCRIPTION OF THE PREFERRED EMBODIMENTS

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

Figure 1:
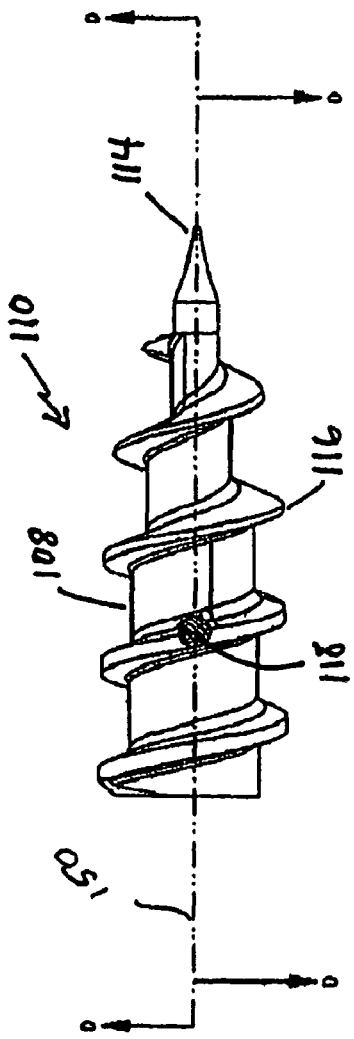
FIG. 1 is a side elevational view of the suture anchor of the present invention.
Figure 3:
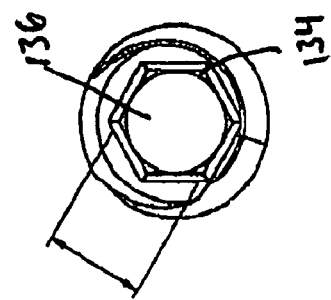
FIG. 3 is a proximal end view of the suture anchor of FIG. 1.

FIG. 1 illustrates a suture anchor according to a first preferred embodiment of the present invention, indicated generally by reference numeral 110. In the preferred embodiment, body 108 of anchor 110 generally tapers to a narrow point 114 at the distal end thereof. In particular, the major diameter of the anchor body is generally constant along about two-thirds of the length of the body, whereupon the diameter of the anchor then tapers to a relatively sharp point, e.g., approximately 16°. The relatively sharp distal tip of anchor 110 enables the anchor to be installed without having to first drill a hole in the bone where the anchor 110 is to be installed.

Although such tapering is preferred, suture anchor 110 may be formed to have a less tapered shape, or even cylindrical shape, to accommodate different preferences of the surgeon and/or the application of the suture anchor. For example, the tapered distal end of the anchor may be formed to be more blunt, in which case it is necessary to provide a pre-formed hole in the bone prior to insertion of the suture anchor.

A continuous thread 116 wraps around the body 108 in a clockwise direction, as shown. Anchor 110 has about five flights of thread, with the angle of the threads and other configurations of the anchor being similar to the suture anchor of U.S. Pat. No. 6,511,499, the disclosure of which is hereby incorporated by reference in its entirety.

Figure 2:
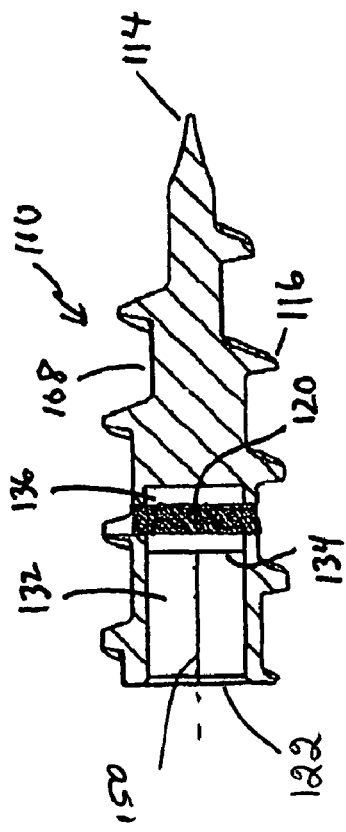
FIG. 2 is a longitudinal sectional view of the suture anchor shown in FIG. 1 through the plane D-D indicated therein.

As can be seen more clearly with reference to FIG. 2, the proximal end portion of the anchor has a hexagonally shaped bore 132 having an opening 122 at the proximal end of anchor body 108 and extending into the anchor body approximately one-third of the length thereof. Prior art anchors have sharp edges around the drive opening, which is problematic in that sutures passing through the central opening at the proximal end of the anchor can be abraded by the sharp edges, thereby compromising the strength of the sutures. The hexagonally shaped bore 132 includes at least two internal faces (not numbered). The two internal faces intersect obliquely relative to each other. In one example, there are six internal planar faces. In the suture anchor of the present invention, the peripheral edges defining hexagonally shaped opening 122 is smooth and rounded outwardly with no sharp edges. Preferably, the opening 122 forms a slight lip curving around the diameter of the bore 132. Thus, sutures threaded through the anchor 110, as will be discussed below, will not become frayed upon being pressed or rubbed against the anchor at the proximal opening 122.

A cylindrical bore 136 having a diameter corresponding to that of the hexagonally shaped bore 132 extends from the distal end of the hexagonally shaped bore 132 to a position roughly halfway along the length of anchor body 108. The transition between hexagonally shaped bore 132 and cylindrical bore 136 forms an annular shoulder 134, against which the distal end 214 of a hex driver 202 abuts when inserted into the hexagonally shaped bore 132 to drive the anchor into bone.

Two longitudinal, diametrically opposite apertures 118 are formed in anchor body 108, the apertures 118 supporting a metal transverse anchor pin 120 which extends across cylindrical bore 136.

As can be seen in FIGS. 1, 2 and 4, apertures 118 extend through and interrupt the threads 116 around anchor body 108 at approximately one-third of the length of the anchor body from the distal end thereof. One or more sutures 200 are secured to the anchor by looping the suture(s) around metal anchor pin 120 as shown in FIG. 4. Although the metal anchor pin 120 is illustrated in FIGS. 2 and 4 as oriented transversal to longitudinal axis 150 of the anchor body 108, the metal anchor pin 120 may form any angle with the longitudinal axis 150 and, thus, the invention is not limited to metal anchor pin 120 forming an angle of about ninety degrees with the longitudinal axis 150 of the anchor body 108.

Preferably, suture anchor 110 is formed of a hard biocompatible metal, such as a titanium alloy, but can be made of biocompatible materials other than metal. The suture secured to the anchor may be FiberWire suture, sold by Arthrex, Inc. of Naples, Fla.

The suture anchor according to the present invention need not be formed as a threaded device, but can also be formed as a tap-in type anchor. Also, the measurements, angles and ratios between the dimensions of the suture anchor may be varied from those described above so as to be suitable for the conditions and applications in which the suture anchor is to be used.

In manufacturing the suture anchor 110 in accordance with the present invention, the anchor body 108 is cast in a die, with the bores, passageways and apertures described above either being formed during the casting process or formed afterwards. If necessary, the distal tip 114 of the anchor 110 is trimmed to the desired length and the surfaces of the anchor are polished to the desired finish.

As mentioned above, the suture anchor of the present invention may be installed in the bone without the need to pre-drill a hole in the bone. The suture anchor is installed using a driver having a shaft having a hexagonal cross-section for at least a length equal to the length of the hexagonal bore 132 from proximal opening 122 to the shoulder 134 inside the anchor 110. The driver has a cannula extending through the entire length thereof, with openings at the proximal and distal ends thereof. Of course, the outer diameter of the hexagonal shaft is sized to fit inside the hexagonal bore in the anchor so as to be enabled to drive the same.

Figure 6:
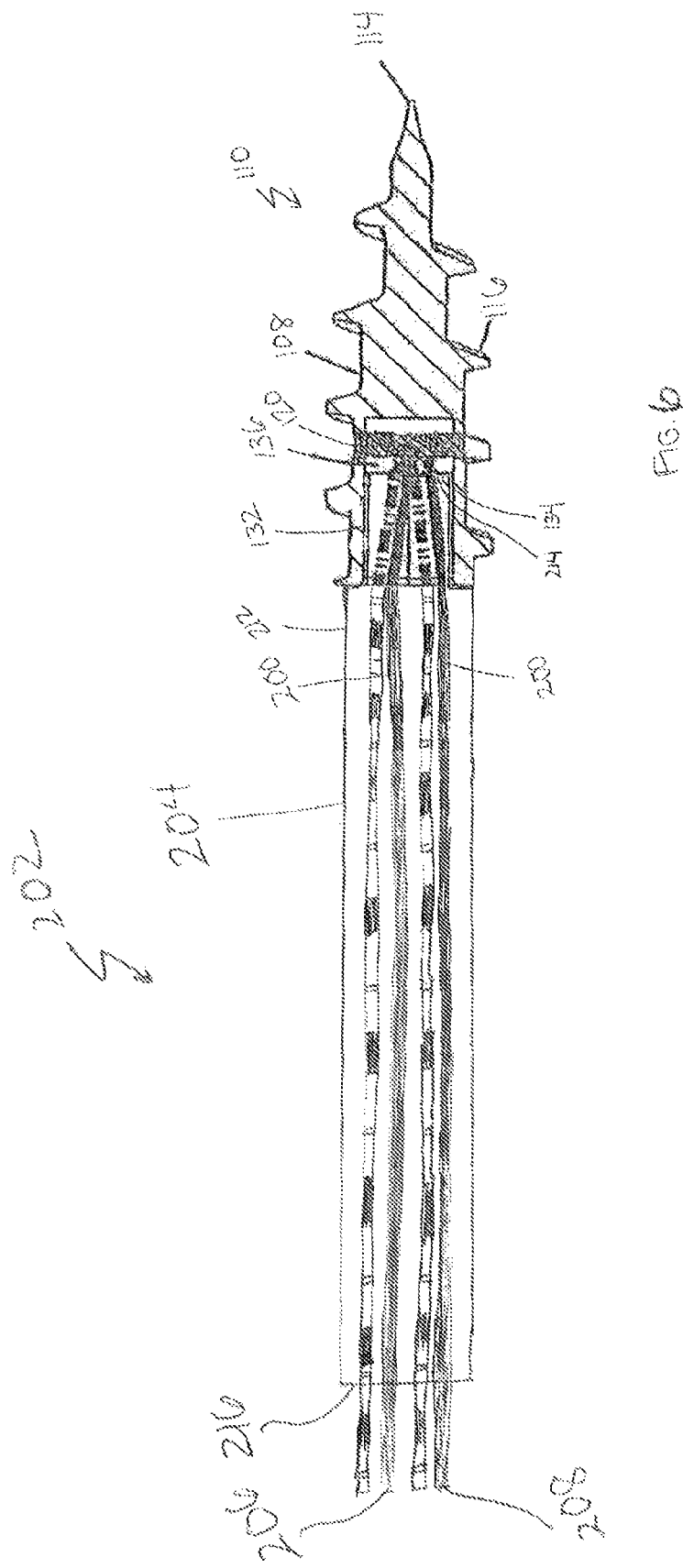
FIG. 6 is a cross sectional view of the suture anchor of FIG. 1 showing more of the hex driver inserted into a hexagonally shaped bore.

As shown in FIGS. 5 and 6, the desired number of suture strands 200 threaded around the anchor pin 120 in the suture anchor 110, the ends 206 and 208 of the suture strands 200 are threaded through the cannula 204 in the hex driver 202 from the distal end 214 thereof and extend from the proximal opening 216 thereof. The distal end 214 of the hex driver 202 is inserted into the proximal end of the anchor 110. With the distal end 214 of the hex driver 202 abutting the shoulder 134 and the anchor 110 positioned at the location at which it is to be installed, the hex driver 202 is rotated to drive the anchor 110 into the bone until the proximal surface of the anchor 110 is flush with the surface of the bone.

Since it is not necessary for the proximal end of the anchor to be countersunk below the bone surface to prevent tissue abrasion by an exposed suture loop, as is required with prior art devices, the suture anchor of the present invention does not need to be inserted as far as the prior art anchors, while also avoiding abrasion of the sutures by the rim of the bone.

The suture anchor of the present invention provides greater pull-out strength of the suture loop than prior suture anchors. In addition, the suture loop of the present invention, being disposed inside the suture anchor, is protected from abrasion and degradation.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A suture anchor assembly for attachment of tissue to bone, the suture anchor assembly comprising:

an anchor body including a distal end, a proximal end, a longitudinal axis, an outer surface and a central bore, the central bore being located at the proximal end and extending partially through the anchor body;

a rigid member having a longitudinal axis and disposed in the central bore, wherein the longitudinal axis of the rigid member extends across the longitudinal axis of the anchor body;

at least one tissue securing suture looped around the rigid member including a first end and a second end, wherein the first end and the second end of the at least one tissue securing suture extend out of the anchor body and extend out of an opening at the proximal end of the anchor body; and a driver having a cannula, wherein the driver is received in a portion of the central bore, wherein the cannula has a distal opening and a proximal opening, wherein the first end and the second end of the at east one tissue securing suture extend out of the proximal opening of the cannula.

2. The suture anchor assembly according to claim 1, wherein the anchor body is metal.

3. The suture anchor assembly according to claim 1, wherein the rigid member is metal.

4. The suture anchor assembly according to claim 1, wherein the anchor body is tapered.

5. The suture anchor assembly according to claim 1, wherein the anchor body is self-tapping.

6. The suture anchor assembly according to claim 1, wherein the anchor body comprises a plurality of threads extending from the outer surface of the anchor body, and the plurality of threads extend to the proximal end of the anchor body.

7. The suture anchor assembly as recited in claim 1, wherein the central bore includes a first section and a second section, the first section accommodates the driver, and the rigid member is disposed in the second section.

8. The suture anchor assembly according to claim 7, wherein the first section has a hexagonally shaped cross section, the second section is cylindrical, and the at least one tissue securing suture is looped around and contacts the rigid member in the second section of the central bore.

9. The suture anchor assembly according to claim 1, wherein the central bore has a cross-sectional shape so as to accommodate the driver for driving the anchor body, the central bore includes a plurality of contact surfaces for the driver, the plurality of contact surfaces including a first planar face and a second planar face, and the first planar face and the second planar face intersect along the longitudinal axis of the anchor body.

10. The suture anchor assembly according to claim 9, wherein the central bore includes a first section and a second section, the first section includes the first planar face and the second planar face that accommodates the driver, and the rigid member is disposed in the second section.

11. The suture anchor assembly according to claim 10, wherein the first section has a hexagonally shaped cross section and the second section is cylindrical, and the at least one tissue securing suture is looped around and contacts the rigid member in the second section of the central bore.

12. The suture anchor assembly according to claim 9, wherein the first planar face and the second planar face are generally parallel to the longitudinal axis of the anchor body.

13. The suture anchor assembly as recited in claim 1, wherein the central bore has a cross-sectional shape so as to accommodate the driver for driving the suture anchor.

14. The suture anchor assembly as recited in claim 1, wherein the longitudinal axis of the rigid member is transverse to the longitudinal axis of the anchor body.

15. The suture anchor assembly as recited in claim 14, wherein the longitudinal axis of the rigid member is generally perpendicular to the longitudinal axis of the anchor body.

16. The suture anchor assembly as recited in claim 1, wherein the first end of the at least one tissue securing suture is unattached to the second end of the at least one tissue securing suture.

17. The suture anchor assembly as recited in claim 1, wherein the first end of the at least one tissue securing suture is free to move relative to the second end of the at least one tissue securing suture.

18. The suture anchor assembly as recited in claim 1, wherein the first end is a first loose end of the at least one tissue securing suture and the second end is a second loose end of the at least one tissue securing suture.

19. The suture anchor assembly as recited in claim 1, wherein the at least one tissue securing suture is slidably releasable from the rigid member.

20. The suture anchor assembly according to claim 1, wherein the rigid member is straight.

* * * * *

UNITED STATES PATENT AND TRADEMARK OFFICE
CERTIFICATE OF CORRECTION

PATENT NO. : 8,343,186 B2
APPLICATION NO. : 11/097172
DATED : January 1, 2013
INVENTOR(S) : Dreyfuss et al.

It is certified that error appears in the above-identified patent and that said Letters Patent is hereby corrected as shown below:

IN THE CLAIMS:

Claim 1, Column 5, line 14: "east" should read as --least--

Signed and Sealed this
Fifth Day of March, 2013

Teresa Stanek Rea
*Acting Director of the United States Patent and Trademark Office*